United States Patent [19]

Cross et al.

[11] Patent Number: 4,602,016

[45] Date of Patent: Jul. 22, 1986

[54] N-(PHENOXYALKYL)IMIDAZOLES AS SELECTIVE INHIBITORS OF THE THROMBOXANE SYNTHETASE ENZYME AND PHARMACEUTICAL COMPOSITIONS THEREOF

[75] Inventors: Peter E. Cross, Canterbury; Roger P. Dickinson, Dover, both of England

[73] Assignee: Pfizer Inc., New York, N.Y.

[21] Appl. No.: 95,755

[22] Filed: Nov. 19, 1979

[30] Foreign Application Priority Data

Dec. 13, 1978 [GB] United Kingdom ............... 48367/78

[51] Int. Cl.[4] .................. A61K 31/415; A61K 27/00; A61K 31/445; C07D 233/54
[52] U.S. Cl. ..................................... 514/234; 548/341; 548/336; 544/139; 546/210; 514/326; 514/240; 514/397; 514/399
[58] Field of Search ................ 548/341, 336; 544/139; 546/210; 424/273 R, 248.58, 267; 514/326, 234, 240, 397, 399

[56] References Cited

U.S. PATENT DOCUMENTS 3,534,061 10/1970 Black ................................ 260/326.5
4,078,071 3/1978 Walker ............................ 424/273 R

OTHER PUBLICATIONS

Moncada et al., Prostaglandins, vol. 13, pp. 611–618 (1977).
Needleman et al., Proc. Natl. Acad. Sci., USA, vol. 74, pp. 1716–1720 (1977).
Tai et al., Biochem. Biophys. Res. Commun., vol. 80, pp. 236–242 (1978).
Yoshimoto et al., Prostaglandins, vol. 16, pp. 529–540 (1978).

Primary Examiner—Henry R. Jiles
Assistant Examiner—Robert C. Whittenbaugh
Attorney, Agent, or Firm—Charles J. Knuth; Albert E. Frost; Robert K. Blackwood

[57] ABSTRACT

N-(mono or disubstituted phenoxyalkyl)imidazoles and the pharmaceutically acceptable acid addition salts thereof are able to selectively inhibit the action of the thromboxane synthetase enzyme without significantly inhibiting the action of the prostacycline synthetase or cyclooxygenase enzymes and are thus useful in the treatment of ischaemic heart disease, stroke, transient ischaemic attack, thrombosis, migraine, and the vascular complications of diabetes.

9 Claims, No Drawings

N-(PHENOXYALKYL)IMIDAZOLES AS SELECTIVE INHIBITORS OF THE THROMBOXANE SYNTHETASE ENZYME AND PHARMACEUTICAL COMPOSITIONS THEREOF

BACKGROUND

This invention relates to imidazole derivatives and in particular to certain N-(phenoxyalkyl)imidazoles substituted in the phenyl ring with acidic and polar groupings. Such compounds are able to selectively inhibit the action of the thromboxane synthetase enzyme without significantly inhibiting the action of the prostacyclin synthetase or cyclo-oxygenase enzymes. The compounds may thus be useful in, for example, the treatment of thrombosis, ischaemic heart disease, stroke, transient ischaemic attack migraine, and the vascular complications of diabetes.

SUMMARY

The compounds of the invention have the general formula:

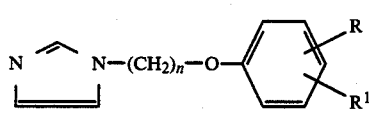

(I)

wherein

R is $NO_2$, CN, $SO_2NH_2$, $C_1$-$C_4$ alkanoyl, $CO_2R^2$, $CH_2CO_2R^2$, $OCH_2CO_2R^2$, $CONHR^3$, $CH_2CONHR^3$, $OCH_2CONHR^3$, $CON(R^4)_2$, $CH_2CON(R^4)_2$, $OCH_2CON(R^4)_2$, $NHR^5$, $CH_2NHR^5$, tetrazolyl, $CH_2$-tetrazolyl and $OCH_2$-tetrazolyl;

$R^1$ is H, $C_1$-$C_4$ alkyl, $C_1$-$C_4$ alkoxy or halogen;

$R^2$ is H or $C_1$-$C_4$ alkyl;

$R^3$ is H, $C_1$-$C_4$ alkyl, $C_1$-$C_4$ alkanoyl, $C_1$-$C_4$ alkylsulphonyl, CN, benzoyl or benzenesulphonyl; the phenyl ring in said benzoyl or benzenesulphonyl group being optionally substituted with one or more $C_1$-$C_4$ alkyl, $C_1$-$C_4$ alkoxy or $CF_3$ groups or halogen atoms; each $R^4$ is $C_1$-$C_4$ alkyl or the two $R^4$ groups together with the nitrogen atom to which they are attached form a pyrrolidone, piperidino or morpholino group;

$R^5$ is H, $C_1$-$C_4$ alkanoyl, $C_1$-$C_4$ alkoxycarbonyl, carbamoyl, $C_1$-$C_4$ alkylcarbamoyl;

and n is 2 or 3;

and the pharmaceutically acceptable acid addition salts thereof.

The invention also includes a pharmaceutical composition comprising a compound of the formula (I), or a pharmaceutically acceptable salt thereof, together with a pharmaceutically acceptable diluent or carrier.

The invention also provides a method of inhibiting the action of the thromboxane synthetase enzyme in an animal, including a human being, without significantly inhibiting the action of the prostacyclin synthetase or cyclo-oxygenase enzymes, which comprises administering to the animal an effective amount of a compound of the formula (I), or a pharmaceutically acceptable salt thereof, or a pharmaceutical composition comprising such a compound or salt together with a pharmaceutically acceptable diluent or carrier.

Pharmaceutically acceptable acid addition salts of the compounds of the invention are salts with acids containing pharmaceutically acceptable anions, e.g. the hydrochloride, hydrobromide, sulphate or bisulphate, phosphate or acid phosphate, acetate, maleate, fumarate, lactate, tartrate, citrate, gluconate, succinate and p-toluene sulphonate salts.

In this specification "halogen" indicates fluorine, chlorine, bromine or iodine. Alkyl and alkoxy groups having 3 or more carbon atoms may be straight or branched chain. Alkanoyl groups having 4 carbon atoms may be straight or branched chain.

Preferred compounds of the invention are those in which n is 2, those in which $R^1$ is H and those in which R is a carboxy, a carbamoyl or an N-(mono or di-methyl)-carbamoyl group (particularly at the 4-position) and $R^1$ is hydrogen. Particularly preferred individual compounds are: 1-[2-(4-carbamoylphenoxy)ethyl]imidazole, 1-[2-(4-N-methylcarbamoylphenoxy)ethyl]imidazole, 1-[2-(4-N,N-dimethylcarbamoylphenoxy)ethyl]imidazole, and 1-[2-(4-carboxyphenoxy)ethyl]imidazole, the latter compound being particularly preferred.

DETAILED DESCRIPTION

The compounds of the invention may be prepared by a number of different routes. In one process according to the invention the compounds are prepared by reacting imidazole with an alkali metal hydride and adding a compound of the formula:

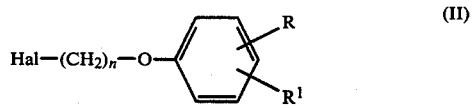

(II)

wherein R and $R^1$ are as previously defined and Hal means chlorine, bromine or iodine.

The reaction is conveniently performed by adding one equivalent of the alkali metal hydride, e.g. sodium hydride, to a solution of imidazole in a dry inert organic solvent, e.g. N,N-dimethylformamide, dimethylsulphoxide or hexamethylphosphoramide. The solution is preferably cooled during the initial stages of the addition but the reaction is generally warmed to 100° C. for 10-15 minutes to complete the reaction when the addition of the alkali-metal hydride is complete. The solution is then cooled and the halide (II) is added, preferably an amount of one equivalent or a slight excess as a solution in the same solvent.

The reaction may be allowed to proceed to completion at room temperature but it is generally preferable to warm the reaction mixture, e.g. to 100° C. to accelerate the reaction. Under these conditions the reaction is usually substantially complete within 10 hours. The reaction product is worked up in a conventional manner, e.g. by removal of the solvent under vacuum, solvent extraction and recrystallisation.

Naturally certain of the groups R may be obtained by chemical transformation reactions and these possibilities will be well known to those skilled in the art. Thus for example, compounds of the formula (I) wherein R is an amino group may conveniently be prepared by reduction of the corresponding compound of formula (I) wherein R is a nitro group. This reduction is readily accomplished by catalytic hydrogenation over a metal catalyst for example using Raney nickel, in a reaction inert organic solvent at room temperature or, alternatively, by using iron powder in hydrochloric acid. Similarly reduction of a compound of the formula (I) wherein R is a cyano group, e.g. using lithium aluminium hydride, yields the corresponding compound of formula (I) wherein R is an aminomethyl group.

The amines so produced may naturally be converted to a variety of N-substituted derivatives of conventional reactions. Thus compounds of the formula (I) wherein R is an amino or aminomethyl group may be converted to compounds wherein R is a group $NHR^5$ or $CH_2NHR^5$ and $R^5$ is formyl, $C_2$-$C_4$ alkanoyl, alkoxycarbonyl, carbamoyl or alkylcarbamoyl by reaction with an appropriate formylating agent, acylating agent, alkyl-chloroformate, potassium cyanate or an alkyl isocyanate respectively. Thus for example reaction of the aminomethyl substituted derivative with acetic anhydride in acetic acid gives the corresponding compound wherein R is —$CH_2NHCOCH_3$; similarly reaction of an amine derivative where R is $NH_2$ with potassium cyanate gives the corresponding ureido derivative where R is —$NHCONH_2$.

Hydrolysis of a compound of the formula (I) wherein R is a cyano group with alkaline hydrogen peroxide can be used to yield a carbamoyl derivative wherein R is $CONH_2$, or, alternatively more vigorous hydrolysis of the nitrile or carbamoyl derivative gives the corresponding acid wherein R is a carboxyl group. Acids may also be obtained by a conventional acid or base catalysed hydrolysis of the corresponding esters, i.e. where R is a group $CO_2R^2$, $CH_2CO_2R^2$ or $OCH_2CO_2R^2$ and $R^2$ is a $C_1$ to $C_4$ alkyl group, e.g. using aqueous sodium hydroxide or hydrochloric acid.

The acids may be converted to a variety of derivatives by conventional methods. Thus formation of the acid chloride e.g. by reaction with thionyl chloride, followed by reaction with ammonia gives the amides where R is $CONH_2$. Similarly reaction of the acid chloride with a $C_1$-$C_4$ lower alkylamine gives compounds where R is $CONHR^3$ and $R^3$ is a $C_1$-$C_4$ alkyl group or, reaction with a di-lower alkylamine, or with pyrrolidine, piperidine or morpholine gives compounds where R is $CON(R^4)_2$.

The amides where R is $CONH_2$, $CH_2CONH_2$ or $OCH_2CONH_2$ may also be obtained from the corresponding esters where R is $CO_2R^2$ $CH_2CO_2R^2$ or $OCH_2CO_2R^2$ respectively, (particularly where $R^2$ is methyl or ethyl) by treating with concentrated aqueous ammonia solution. Again these compounds may be further reacted to give compounds of the formula (I) wherein R is $CONHR^3$, $CH_2CONHR^3$ or $OCH_2CONHR^3$ and $R^3$ is alkanoyl, alkylsulphonyl, benzoyl or benzene sulphonyl by conventional methods. Thus the carbamoyl derivatives where R is $CONHR^3$, $CH_2CONHR^3$ or $OCOCHNHR^3$ and $R^3$ is a $C_1$-$C_4$ alkanoyl group may be prepared by an acylation reaction, e.g. using the imidazolide derivative prepared from a $C_1$-$C_4$ alkanoic acid by reaction with N,N'-carbonyldiimidazole. A similar reaction may be used to prepare compounds where $R^3$ is benzoyl, i.e. using benzoic acid and N,N'-carbonyldi-imidazole. The compounds where $R^3$ is cyano or an alkylsulphonyl or benzenesulphonyl group may similarly be prepared by reacting the corresponding acid where R is $CO_2H$, $CH_2CO_2H$ or $OCH_2CO_2H$ with N,N'-carbonyldiimidazole and addinhg cyanamide or the required alkylsulphonamide or benzene sulphonamide, the product in this case being isolated in its tautomeric form, i.e. as a carboximidic acid derivative. Compounds where $R^1$ is a sulphonamido group may be prepared from the unsubstituted compound of formula (I) wherein R is hydrogen by a chlorosulphonylation reaction, e.g. by reaction with chlorosulphonic acid and phosphorus pentachloride, followed by treatment with concentrated aqueous ammonia solution. Compounds where R is or contains a tetrazolyl group are prepared from the corresponding cyano derivative by reaction with sodium azide and ammonium chloride.

All the above transformation reactions are quite conventional and conditions for their performance will be well known to those skilled in the art as will other possibilities and variations.

The starting materials of formula (II) are generally known compounds. They may be prepared from an appropriately substituted phenol via reaction with sodium hydride and an arylsulphonyloxy ethyl or propyl halide to give the compounds of formula (II) wherein n is 2 or 3 respectively.

The compounds of formula (I) have been found to selectively inhibit the action of the thromboxane synthetase enzyme without significantly affecting the action of the prostacyclin synthetase or cylo-oxygenase enzymes. Thus the compounds are of value in the treatment of a variety of clinical conditions which are characterised by an imbalance of prostacyclin/thromboxane $A_2$. For the reasons given below these conditions may include thrombosis, ischaemic heart disease, stroke, transient ischaemic attack, migraine and the vascular complications of diabetes.

Research work has established that in most tissues the major product of the arachidonic acid metabolism is either of two unstable substances, thromboxane $A_2$ ($TxA_2$) or prostacyclin ($PGI_2$). (Proc. Nat. Acad. Sci. U.S.A., 1975, 72, 2994; Nature, 1976, 263, 663; Prostaglandins, 1976, 12, 897). In most cases the prostaglandins $PGE_2$, $PGF_{2\alpha}$ and $PGD_2$ are comparatively minor by-products in this bio-synthetic pathway. The discovery of thromboxane $A_2$ and prostacyclin has significantly increased our understanding of vascular homeostasis; prostacyclin for instance is a powerful vasodilator and inhibitor of platelet aggregation, and in this last respect is the most potent endogenous substance so far discovered. The prostacyclin synthetase enzyme is located in the endothelial layer of the vasculature, and is fed by endoperoxides released by blood platelets coming into contact with the vessel wall. The prostacyclin thus produced is important for prevention of platelet deposition on vessel walls. (Prostaglandins, 1976, 12, 685; Science, 1976, 17; Nature, 1978, 273, 765).

Thromboxane $A_2$ is synthetised by the thromboxane synthetase enzyme which is located in, for example, the blood platelets. Thromboxane $A_2$ is a powerful vasoconstrictor and pro-aggregatory substance. As such its actions are in direct opposition to those of prostacyclin. If, for any reason, prostacyclin formation by the vaculature is impaired, then the endoperoxides produced by platelets coming into contact with the vessel wall are converted into thromboxane, but are not converted effectively into prostacyclin (Lancet, 1977, 18; Prostaglandins, 1978, 13, 3). Alteration of the prostacyclin/thromboxane balance in favour of the latter substance could result in platelet aggregation, vasosprasm (Lancet, 1977, 479; Science, 1976, 1135; Amer. J. Cardiology, 1978, 41, 787) and an increased susceptibility to atherothrombosis (Lancet (i) 1977, 1216). It is also known that in experimental atherosclerosis prostacyclin generation is suppressed and thromboxane $A_2$ production is enhanced (Prostaglandins, 1977, 14, 1025 and 1035). Thus thromboxane $A_2$ has been implicated as the causative agent in variant angina, myocardial infarction, sudden cardiac death and stroke (Thromb. Haemostasis, 1977, 38, 132). Studies in rabbits have shown that ECG changes typical of these conditions were produced when freshly prepared thromboxane A₂ was injected directly into the animal's heart (Biochem. Aspects of Prostaglandins and Thromboxanes, Editors, N. Kharasch and J. Fried, Academic Press 1977 page 189). This technique is considered to represent a unique animal model of the heart attacks of coronary patients and has been used to show that administration of a compound believed to antagonise the effects of thromboxane $A_2$ protects the rabbits from the adverse consequences of thromboxane $A_2$ injection.

Another area where a $PGI_2/TxA_2$ imbalance is considered to be a contributory factor is that of migraine. The migraine headache is associated with changes in intra and extra-cerebral blood flow, in particular a pre-headache reduction of cerebral blood flow followed by dilation in both vascular areas during the headache phase.

Prior to the development of the headache, blood levels of 5-hydroxytryptamine are elevated, and this suggests the occurrence of in vivo aggregation and release of the amine from the platelet stores. It is known that the blood platelets of migraine patients are more prone to aggregate than are those of normal individuals (J.clin.Pathol., 1971, 24, 250; J.Headache, 1977, 17, 101). Furthermore, it has now been postulated that not only is an abnormality of platelet function a major factor in the pathogenesis of migraine attacks but it is in fact their prime cause (Lancet (i), 1978, 501). Thus a drug that selectively modifies platelet function to inhibit thromboxane $A_2$ formation could be of considerable benefit in migraine therapy.

Abnormalities of platelet behaviour have been reported in patients with diabetes mellitus (Metabolism, 1979, 28, 394; Lancet, 1978 (i) 235). Diabetic patients are known to be particularly susceptible to microvascular complications, atherosclerosis and thrombosis and platelet hyper-reactivity has been suggested as the cause of such angiopathy. Diabetic platelets produce elevated amounts of $TxB_2$ and malondialdehyde (Symposium "Diabetes and Thrombosis-Implications for Therapy", Leeds, U.K., April 1979). Also, it has been shown that in rats with experimental diabetes vascular prostacyclin production is impaired and $TxA_2$ synthesis from the platelets is elevated (IV International Prostaglandin Conference, Washington, D.C. May, 1979). Thus the imbalance between prostacyclin and $TxA_2$ is considered to be responsible for the microvascular complications of diabetes. A $TxA_2$-synthetase inhibitor could therefore find clinical utility in preventing these vascular complications.

Aspirin and most other non-steroidal anti-inflammatory drugs inhibit the cyclo-oxygenase enzyme. The effect of this is to shut down the production of the $PGG_2/H_2$ endoperoxides and by so doing to reduce both the prostacyclin and thromboxane $A_2$ levels. Aspirin and aspirin-like drugs have been evaluated clinically for prevention of stroke and heart attack (New England J.Med., 1978, 299, 53; B.M.J., 1978, 1188; stroke, 1977, 8 301).

Although some encouraging results have been obtained with these drugs, a compound which specifically inhibits thromboxane $A_2$ formation leaving the biosynthesis of prostacyclin unimpaired would be more valuable in these clinical conditions (Lancet, (ii), 1978, 780).

The effect of the compounds of the formula (I) on the thromboxane synthetase enzyme, and the prostacyclin synthetase and cyclo-oxygenase enzymes has been measured by the following in vitro enzyme assays:

1. Cyclo-oxygenase

Ram seminal vesicle microsomes (Biochemistry, 1971, 10, 2372) are incubated with arachidonic acid (100 µM; 1 min.: 22°) to produce $PGH_2$ and aliquots of the reaction mixture injected into a stream of Krebs-bicarbonate at 37° C. (containing a mixture of antagonists (Nature, 1978, 218, 1135) and indomethacin (Brit. J. Pharmacol., 1972, 45, 451) which is superfusing a spirally-cut rabbit aorta strip (Nature, 1969, 233, 29). The ability of a compound to inhibit the enzyme is measured by comparing the increases in isometric tension produced by $PGH_2$ in the absence of the test compound, and following preincubation of the enzyme with the test compound for 5 minutes.

2. Prostacyclin (PGI₂) Synthetase

Pig aorta microsomes (Nature, 1976, 263, 663) are incubated (30 sec.; 22° C.) with $PGH_2$ produced as in (1) and aliquots bio-assayed as in 1. $PGI_2$ production is assessed indirectly by measuring the decrease in $PGH_2$-induced tension ($PGI_2$ itself does not contract the aorta). This decrease can be prevented completely by pre-incubation of the enzyme with the selective $PGI_2$ synthetase inhibitor, 15-hydroperoxy-arachidonic acid (Prostaglandins, 1976, 12, 715). The test compound is then pre-incubated with the enzyme for 5 minutes, and its ability to prevent the decrease in tension is measured.

3. Thromboxane $A_2$ (TxA₂) Synthetase

Indomethacin pretreated human platelet microsomes (Science 1976, 193, 163) are incubated (2 min.: 0° C.) with $PGH_2$ (produced as in 1) and aliquots of the reaction mixture superfused over two rabbit aorta spirals which are separated by a delay coil (2 min.). The latter is required to allow the selective decay of the more unstable thromboxane $A_2$ (Proc. Nat. Acad. Sci., 1975, 72, 2994) thereby enabling the separate measurement of increased isometric tension due to the $TxA_2$ formed and the $PGH_2$ remaining. The test compound is pre-incubated with the enzyme for 5 minutes, and its ability to inhibit the thromboxane synthetase enzyme is measured as its reduction of the $TxA_2$ component of the isometric tension.

Compounds of the invention tested in this way have been shown to be capable of selectively inhibiting the thromboxane synthetase enzyme. The results of these tests are shown in the following Table, which gives the molar concentration of each compound which caused a 50% change in the effect of the relevant enzyme on isometric tension, i.e. caused a 50% inhibition of the action of that enzyme. Also shown are the ratios of molar concentrations causing 50% inhibition of the actions of the prostacyclin synthetase and thromboxane synthetase enzymes, which gives an indication of the ability of compounds to selectively inhibit the action of the latter enzyme relative to the former.

| Example No. | (1) thromboxane synthetase | (2) cyclo-oxygenase | (3) prostacyclin synthetase | Ratio of (3) to (1) |
|---|---|---|---|---|
| 1 | $2.2 \times 10^{-8}$ | $>10^{-4}$ | $>10^{-4}$ | >4,500 |
| 2 | $1.0 \times 10^{-5}$ | | | |
| 3 | $1.0 \times 10^{-6}$ | | | |
| 4 | $4.0 \times 10^{-8}$ | | $>10^{-4}$ | >2,500 |
| 7 | $4.6 \times 10^{-8}$ | | $1 \times 10^{-4}$ | 2,200 |
| 8 | $3.4 \times 10^{-8}$ | | $>10^{-4}$ | >2,900 |
| 16 | $3.8 \times 10^{-10}$ | $>10^{-4}$ | $>10^{-4}$ | >260,000 |
| 17 | $3.4 \times 10^{-5}$ | | | |
| 18 | $4.2 \times 10^{-9}$ | | | |
| 19 | $5.8 \times 10^{-7}$ | | | |
| 21 | $1.2 \times 10^{-8}$ | | | |
| 22 | $4.9 \times 10^{-9}$ | | | |
| 23 | $1.6 \times 10^{-8}$ | | | |
| 24 | $5.0 \times 10^{-9}$ | $>10^{-4}$ | $>10^{-4}$ | >20,000 |
| 25 | $5.6 \times 10^{-9}$ | $>10^{-4}$ | $>10^{-4}$ | >18,000 |
| 26 | $1.0 \times 10^{-5}$ | | | |
| 39 | $6.6 \times 10^{-6}$ | | | |

The results given in the Table show that all of the compounds tested caused a 50% inhibition of the thromboxane synthetase enzyme at a molar concentration of $1.0 \times 10^{-5}$ or less, and several caused 50% inhibition at concentrations of $10^{-8}$ or less.

Of the compounds tested for inhibition of the cyclooxygenase enzyme, none caused 50% inhibition at a molar concentration of $10^{-4}$ or less, their ability to inhibit that enzyme being at least 4,500 times less, and in several cases more than 10,000 times less, than their ability to inhibit the thromboxane synthetase enzyme.

Of the compounds tested for inhibition of the prostacyclin synthetase enzyme, none caused 50% inhibition at a molar concentration less than 2,000 times greater than that at which they caused 50% inhibition of the thromboxane synthetase enzyme, i.e. they were all at least 2,000 times more potent as inhibitors of thromboxane synthetase than of prostacyclin synthetase.

In addition to the above an in vitro assay for measuring the inhibition of human blood platelet aggregation has been described and this may be predictive of anti-thrombotic efficacy clinically (Lancet (ii), 1974, 1223; J. Exp. Med., 1967, 126, 171). Both the clinically effective agents aspirin and sulphinpyrazone show inhibitory activity in vitro against a variety of aggregating agents in this test.

A number of in vivo tests in animals have also been described for evaluating potential anti-thrombotic drugs. Intravenous injection of arachidonic acid causes death in rabbits by causing platelet clumping and embolisation in the lungs. Again both the clinically effective aspirin (Agents and Actions, 1977, 1, 481) and sulphinpyrazone (Pharmacology, 1976, 14, 522) protect the rabbit from the lethal effect of the injection. Sulphinpyrazone has also been shown to prevent the aggregation of platelets in an extra corporeal loop of the abdominal aorta of rats in vivo (Thromb. Diathes. Haem., 1973, 30, 138). The compound of Example 16 has been tested by the above methods and found to be effective in preventing human blood platelet aggregation, in protecting rabbits from the lethal effect of arachidonic acid injection and in preventing aggregation of platelets in rat aorta.

The compounds may be administered orally in the form of tablets or capsules containing a unit dose of the compound together with such excipients as maize starch, calcium carbonate, dicalcium phosphate, alginic acid, lactose, magnesium stearate, "Primogel" (Trade Mark) or talc. The tablets are typically prepared by granulating the ingredients together and filling them into hard gelatine capsules of the appropriate size to contain the ingredients.

The compounds may also be administered parenterally, for example by intramuscular, intravenous or subcutaneous injection. For parenteral administration, they are best used in the form of a sterile aqueous solution which may contain other solutes such as tonic and pH adjusters. The compounds may be added to distilled water and the pH adjusted to 3–6 using an acid such as citric, lactic or hydrochloric acid. Sufficient solutes such as dextrose or saline may be added to render the solution isotonic. The resulting solution may then be sterilised and filled into sterile glass vials of an appropriate size to contain the desired volume of solution. The compounds of the invention may also be administered by the infusion of a parenteral formulation as described above into a vein.

For oral administration to human patients, it is expected that the daily dosage level of a compound of the invention will be from 0.1 to 20 mg/kg per day for a typical adult patient (70 kg). For parenteral administration, it is expected that the daily dosage level of a compound of the formula (I) will be from 0.01–0.5 mg/kg per day, for a typical adult patient. Thus tablets or capsules can generally be expected to contain from 5 to 150 mg of the active compound for administration orally up to 3 times a day. Dosage units for parenteral administration can be expected to contain from 0.5–35 mg of the active compound. A typical vial could be a 10 ml vial containing 5 mg of the active compound in 6–10 ml of solution.

It should of course be appreciated that the physician in any event will determine the actual dosage which will be most suitable for the individual and it will vary with the age, weight and response of the patient. The above dosages are exemplary of the average patient, there may of course be individual cases where higher or lower dosage ranges are merited.

The following examples are merely illustrative, and in no way limit the scope of the appended claims.

EXAMPLE 1

1-[2-(4-Carbamoyl phenoxy)ethyl]imidazole

Sodium hydride (14.4 g, 50% suspension in mineral oil) was added cautiously to a stirred and cooled solution of imidazole (20.4 g) in dry N,N-dimethylformamide (100 ml). After the initial vigorous reaction had subsided the mixture was heated to 100° C. for 10 minutes and then stirred at room temperature for a further 1 hour. A solution of 4-(2-chloroethoxy)benzamide (60.0 g) in the minimum volume of N,N-dimethylformamide was added and the mixture was heated at 100° C. for 5.5 hours. The solvent was evaporated and the residue was poured into water. The mixture was extracted several times with chloroform and the combined chloroform extracts were dried ($MgSO_4$) and evaporated to give a mixture of oil and solid. The mixture was triturated with ether and the solid was collected and crystallised from a mixture of methanol and ethyl acetate to give 1-[2-(4-carbamoyl phenoxy)ethyl]imidazole (35.2 g), m.p. 148°–149° C. Found: C, 62.25; H, 5.61; N, 18.54. $C_{12}H_{13}N_3O_2$ requires: C, 62.32; H, 5.67; N, 18.17%.

Compounds prepared similarly, using the appropriately substituted (2-chloro)ethoxy-benzene compound instead of 4-(2-chloroethoxy)benzamide, are listed in Tables I and II.

TABLE I

[Structure: imidazole-N-CH2CH2-O-phenyl-R]

| Example | R | m.p. (°C.) | Recrystallisation Solvent | Analysis % (Theoretical in brackets) C | H | N |
|---|---|---|---|---|---|---|
| 2 | 2-CONH$_2$ | 147–148° | Ethyl Methyl Ketone | 61.94 (62.32 | 5.65 5.67 | 17.87 18.17) |
| 3 | 4-CH$_2$CONH$_2$ | 147–149° | Ethyl Methyl Ketone | 63.64 (63.66 | 6.09 6.16 | 16.94 17.13) |
| 4 | 2-CO$_2$C$_2$H$_5$ | 89–90.5° | Isopropanol | 57.73 (57.44 | 5.34 5.36 | 7.59 7.44)[2] |
| 5 | 3-CN | 126–128° | Isopropanol/ Ethyl Acetate | 58.55 (57.72 | 4.77 4.85 | 16.73 16.83)[1] |
| 6 | 2-CH$_2$CO$_2$C$_2$H$_5$ | 129.5–130.5° | Isopropanol/ Ethyl Acetate | 58.25 (57.97 | 6.21 6.16 | 9.09 9.02)[1] |
| 7 | 3-CH$_2$CO$_2$C$_2$H$_5$ | 130–131° | Methanol/ Ethyl Acetate | 58.24 (58.45 | 5.60 5.68 | 7.44 7.18)[3] |
| 8 | 4-CH$_2$CO$_2$C$_2$H$_5$ | 101.5–103° | Ethyl Acetate | 58.54 (58.45 | 5.68 5.68 | 7.23 7.18)[3] |
| 9 | 4-OCH$_2$CO$_2$C$_2$H$_5$ | 97–98° | Ethyl Acetate | 55.65 (56.15 | 5.64 5.46 | 6.71 6.89)[3] |
| 10 | 4-NO$_2$ | 56–57° | Ethyl Acetate/ Petrol | 56.25 (56.65 | 4.75 4.76 | 17.88 18.02)[4] |
| 11 | 4-NHCOCH$_3$ | 168–170° | Ethyl Acetate | 63.43 (63.66 | 6.13 6.16 | 16.70 17.13) |
| 12 | 4-CN | | | | | |

[1] hydrochloride salt
[2] maleate salt
[3] fumarate salt
[4] Purified by SiO$_2$ chromatography. Elution with ethyl acetate gave 1-(4-N—nitrophenyl)imidazole as by-product. Product eluted with ethyl acetate/MeOH (9:1).

TABLE II

[Structure: imidazole-N-CH2CH2-O-phenyl with R and R$^1$ substituents]

| Example | R | R$^1$ | m.p. (°C.) | Recrystallisation Solvent | Analysis % (Theoretical in brackets) C | H | N |
|---|---|---|---|---|---|---|---|
| 13 | 4-CONH$_2$ | 2-OCH$_3$ | 154–156° | methanol/ethyl acetate | 58.58 (58.75 | 5.61 5.88 | 15.46 15.81) |
| 14 | 4-CO$_2$C$_6$H$_5$ | 2-Cl | 90° | ethyl acetate/ petrol | Not characterised further | | |
| 15 | 5-CO$_2$C$_2$H$_5$ | 2-CH$_3$ | | | | | |

EXAMPLE 16

1-[2-(4-Carboxyphenoxy)ethyl]imidazole

A solution of 1-[2-(4-carbamoylphenoxy)ethyl]imidazole (4.5 g) in 5N hydrochloric acid (20 ml) was heated to 100° C. for 2 hours and then allowed to cool. The resulting solid was filtered off to give 1-[2-(4-carboxyphenoxy)ethyl]imidazole hydrochloride (4.55 g), m.p. 233°–235° C., raised to 239°–241° C. on crystallisation from acetic acid. Found: C, 53.93; H, 4.99; N, 10.91. C$_{12}$H$_{12}$N$_2$O$_3$.HCl requires: C, 53.64; H, 4.88; N, 10.43%.

EXAMPLE 17

1-[2-(2-Carboxyphenoxy)ethyl]imidazole Hydrochloride

A solution of 1-[2-(2-ethoxycarbonyl-phenoxy)ethyl]imidazole (5.1 g) (prepared by treatment of the maleate salt with NaOH followed by extraction with ethyl acetate) in 5N hydrochloric acid (30 ml) was heated on a steam bath for 8 hours and then evaporated. The residue was crystallised from isopropanol to give 1-[2-(2-carboxyphenoxy)ethyl]imidazole hydrochloride (3.08 g), m.p. 138°–139.5°. Found: C, 53.61; H, 4.88; N, 10.46. C$_{12}$H$_{12}$N$_2$O$_3$.HCl requires: C, 53.64; H, 4.88; N, 10.43%.

EXAMPLE 18

4-[2-(1-Imidazolyl)ethoxy]phenoxyacetic acid Hydrochloride

A solution of ethyl 4-[2-(1-imidazolyl)ethoxy]phenoxyacetate (1.6 g) (prepared by treatment of the fumarate salt with NaOH followed by extraction with ethyl acetate) in 5N hydrochloric acid (10 ml) was heated on a steam bath for 18 hours and then evaporated. The residue was crystallised from acetonitrile to give 4-[2-(1-imidazolyl)ethoxy]phenoxyacetic acid hydrochloride (0.72 g), m.p. 162°–164°. Found: C, 52.10; H, 4.96; N, 9.65. $C_{13}H_{14}N_2O_4 \cdot HCl$ requires: C, 52.27; H, 5.06; N, 9.38%.

EXAMPLE 19

2-[2-(1-Imidazolyl)ethoxy]phenylacetic acid Hydrochloride

A solution of ethyl 2-[2-(1-imidazolyl)ethoxy]phenylacetate hydrochloride (3.5 g) in 5N hydrochloric acid (20 ml) was heated on a steam bath for 6 hours and then evaporated. The residue was crystallised from isopropanol to give 2-[2-(1-imidazolyl)ethoxy]phenylacetic acid hydrochloride, m.p. 146°–147°. Found: C, 54.69; H, 5.25; N, 9.80. $C_{15}H_{14}N_2O_3 \cdot HCl$ requires: C, 55.22; H, 5.35; N, 9.91%.

EXAMPLE 20

1-[2-(4-Carboxy-2-chlorophenoxy)ethyl]imidazole

A mixture of 1-[2-(4-ethoxycarbonyl-2-chlorophenoxy)ethyl]imidazole (115 mg) and potassium hydroxide (50 mg) in water (6.25 ml) was heated on a steam bath for 18 hours. The resulting solution was just acidified with acetic acid and evaporated to a small volume. The resulting solid was filtered off, washed with water and crystallised from water to give 1-[2-(4-carboxy-2-chlorophenoxy)ethyl]imidazole (65 mg), m.p. 204° C. Found: C, 53.44; H, 4.15; N, 10.52. $C_{12}H_{11}ClN_2O_3$ requires: C, 54.04; H, 4.16; N, 10.51%.

EXAMPLE 21

1-[2-(3-Carboxyphenoxy)ethyl]imidazole Hydrochloride

A mixture of 1-[2-(3-cyanophenoxy)ethyl]imidazole hydrochloride (2.0 g) and 5N sodium hydroxide was heated on a steam bath for 6 hours to give a clear solution. The solution was acidified with dilute hydrochloric acid and evaporated to dryness. The residue was extracted with hot acetic acid and the solution was filtered and evaporated. The residue was crystallised from acetic acid to give 1-[2-(3-carboxy-phenoxy)ethyl]imidazole hydrochloride, m.p. 232°–233° C. Found: C, 53.13; H, 4.69; N, 10.68. $C_{12}H_{12}N_2O_3 \cdot HCl$ requires: C, 53.64; H, 4.88; N, 10.43%.

EXAMPLE 22

1-[2-(4-Tetrazol-5-ylphenoxy)ethyl]imidazole

A mixture of 1-[2-(4-cyanophenoxy)ethyl]imidazole (2.1 g) sodium azide (3.25 g) and ammonium chloride (2.67 g) in dry N,N-dimethylformamide (25 ml) was heated on a steam bath for 22 hours. The solution was evaporated and the residue was washed with chloroform. The chloroform extract was filtered and evaporated and the residue was crystallised from aqueous ethanol to give 1-[2-(4-tetrazol-5-ylphenoxy)ethyl]imidazole (0.81 g), m.p. 196°–197° C. Found: C, 56.30; H, 4.76; N, 33.20. $C_{12}H_{12}N_6O$ requires: C, 56.24; H, 4.72; N, 32.80%.

EXAMPLE 23

4-[2-(1-Imidazolyl)ethoxy]phenoxyacetamide

A mixture of ethyl 4-[2-(1-imidazolyl)ethoxy]phenoxyacetate free base (1.0 g), ethanol (10 ml) and concentrated ammonia solution (20 ml) was allowed to stand at room temperature for 20 hours to give a clear solution. The solution was evaporated and the residue was crystallized twice from 2-butanone to give 4-[2-(1-imidazolyl)ethoxy]phenoxyacetamide (0.38 g), m.p. 123°–124° C. Found: C, 59.70; H, 5.77; N, 16.26. $C_{13}H_{15}N_3O_3$ requires: C, 59.76; H, 5.79; N, 16.08%.

EXAMPLE 24

1-[2-(4-N-Methylcarbamoylphenoxy)ethyl]imidazole

Thionyl chloride (1.0 ml) was added dropwise to a stirred mixture of 1-[2-(4-carboxyphenoxy)ethyl]imidazole hydrochloride (1.0 g) and dry N,N-dimethylformamide (5 ml) at room temperature. The resulting clear solution was stirred for 5 hours. The solution was then added dropwise to a stirred solution of 40% aqueous methylamine (20 ml) and the resulting mixture was evaporated to dryness. The residue was taken up in water and the solution was made just basic by the addition of sodium bicarbonate. The mixture was evaporated and the residue was extracted with hot ethyl acetate. The extract was filtered and evaporated to give an oil which solidified on standing. The solid was crystallised from ethyl acetate to give 1-[2-(4-N-methylcarbamoylphenoxy)ethyl]imidazole (0.68 g), m.p. 132°–133° C. Found: C, 63.41; H, 6.14; N, 17.24. $C_{13}H_{15}N_3O_2$ requires: C, 63.66; H, 6.16; N, 17.13%.

EXAMPLE 25

1-[2-(4-N,N-Dimethylcarbamoylphenoxy)ethyl]imidazole

Successive treatment of 1-[2-(4-carboxyphenoxy)ethyl]imidazole hydrochloride (1.0 g) with thionyl chloride (1.0 ml) and 50% aqueous dimethylamine (20 ml) as described in Example 24 gave 1-[2-(4-N,N-dimethylcarbamoylphenoxy)ethyl]imidazole isolated as the fumarate salt, m.p. 113°–115° C. (from ethyl acetate). Found: C, 57.11; H, 5.52; N, 11.05. $C_{14}H_{17}N_3O_2 \cdot C_4H_4O_4$ requires: C, 57.59; H, 5.64; N, 11.19%.

EXAMPLE 26

1-[4-(2-Imidazol-1-yl)ethoxybenzoyl]morpholine

Successive treatment of 1-[2-(4-carboxyphenoxy)ethyl]imidazole (1.4 g) with thionyl chloride (1.4 g) and morpholine (10 ml) as described in Example 25 gave N-[4-(2-imidazol-1-yl)ethoxybenzoyl]morpholine, m.p. 109°–111° C. (from ethyl acetate). Found: C, 63.80; H, 6.40; N, 13.87. $C_{16}H_{19}N_3O_3$ requires: C, 63.77; H, 6.36; N, 13.94%.

EXAMPLE 27

1-[2-(4-Sulphamoylphenoxy)ethyl]imidazole

Phosphorus pentachloride (2.08 g) was added cautiously to chlorosulphonic acid (2.91 g) and the resulting solution was cooled to 0° C. 1-(2-Phenoxyethyl)imidazole (1.88 g) was added in portions, allowing the effervescence to subside after each addition. The mixture was heated on a steam bath for 10 minutes, cooled, and poured onto a mixture of crushed ice and excess concentrated ammonia solution. The resulting gummy solid was filtered off, washed with water, sucked as dry as possible at the filter pump and chromatographed on silica gel. Elution with a mixture of chloroform and methanol (4:1) gave a gum which crystallised on trituration with a few mls. of ethanol. The solid was crystallised from ethanol to give 1-[2-(4-sulphamoylphenoxy)ethyl]imidazole (0.5 g), m.p. 147.5°–148.5° C. Found: C, 49.57; H, 4.93; N, 15.36. $C_{11}H_{13}N_3O_3S$ requires: C, 49.42; H, 4.90; N, 15.72%.

EXAMPLE 28

1-[2-(4-Aminophenoxy)ethyl]imidazole

Iron powder (6.0 g) was added in portions to a warm solution of 1-[2-(4-nitrophenoxy)ethyl]imidazole (3.7 g) in 5N hydrochloric acid (60 ml). After 20 minutes the solution was cooled, made basic with dilute sodium hydroxide solution and the mixture was shaken with chloroform and filtered. The chloroform layer of the filtrate was separated, dried ($Na_2SO_4$) and evaporated to give a solid which was crystallised from ethyl acetate/petrol to give 1-[2-(4-aminophenoxy)ethyl]imidazole (2.25 g) m.p. 91°–92° C. Found: C, 64.35; H, 6.40; N, 20.61. $C_{11}H_{13}N_3O$ requires: C, 65.01; H, 6.45; N, 20.68%.

EXAMPLE 29

1-[2-(4-Methoxycarbonylaminophenoxy)ethyl]imidazole

Methyl chloroformate (0.5 g) was added to a stirred solution of 1-[2-(4-aminophenoxy)ethyl]imidazole (1.0 g) in chloroform (50 ml) and the mixture was stirred at room temperature for 2 hours and then evaporated. The residue was dissolved in water and made basic by the addition of sodium bicarbonate. The resulting precipitate was filtered off, washed with water and crystallised from methanol/water to give 1-[2-(4-methoxycarbonylaminophenoxy)ethyl]imidazole (1.13 g), m.p. 152°–153° C., Found: C, 59.77; H, 5.81; N, 15.92. $C_{13}H_{15}N_3O_3$ requires: C, 59.76; H, 5.79; N, 16.08%.

EXAMPLE 30

1-[2-(4-Ureidophenoxy)ethyl]imidazole

1-[2-(4-Aminophenoxy)ethyl]imidazole (0.6 g) was dissolved in 1N hydrochloric acid (3.0 ml) and a solution of potassium cyanate (0.3 g) in 1 ml of water was added. The mixture was allowed to stand at room temperature for 15 minutes and the resulting solid was filtered off, washed with water and crystallised from water to give 1-[2-(4-ureidophenoxy)ethyl]imidazole (0.6 g), m.p. 199°–201° C. Found: C, 58.20; H, 5.70; N, 23.06. $C_{12}H_{14}N_4O_2$ requires: C, 58.52; H, 5.73; N, 22.75%.

EXAMPLE 31

1-[2-(4-Aminomethylphenoxy)ethyl]imidazole dihydrochloride

A solution of 1-[2-(4-cyanophenoxy)ethyl]imidazole (8.6 g) in dry tetrahydrofuran (70 ml) was added dropwise to a stirred suspension of lithium aluminium hydride (3.8 g) in dry tetrahydrofuran (150 ml) at reflux. The mixture was stirred for 3 hours at reflux followed by 18 hours at room temperature. Water (4 ml) was added cautiously followed by 16 ml of 1.25N sodium hydroxide. The mixture was filtered and the filtrate was evaporated to give an oil which was chromatographed on silica gel. Elution of the column with chloroform/methanol (20:1) gave the pure product (5.7 g) as an oil.

A portion of the oil was dissolved in chloroform and treated with an excess of ethereal hydrogen chloride. The solid was filtered off and crystallised from ethanol to give 1-[2-(4-aminomethylphenoxy)ethyl]imidazole dihydrochloride m.p. 216°–217° C. Found: C, 49.34; H, 5.94; N, 14.60. $C_{12}H_{15}N_3O.2HCl$ requires: C, 49.66; H, 5.91; N, 14.48%.

EXAMPLE 32

1-[2-(4-Acetylaminomethylphenoxy)ethyl]imidazole

1-[2-(4-Aminomethylphenoxy)ethyl]imidazole (1.1 g) was heated on a steam bath for 2 hours in a mixture of acetic acid (10 ml) and acetic anhydride (1 ml). The solution was then evaporated and the residue was dissolved in a small volume of water. The solution was made basic with sodium bicarbonate and the resulting solid was filtered off, washed with water and crystallised from water to give 1-[2-(4-acetylaminomethylphenoxy)ethyl]imidazole (0.70 g), m.p. 115°–166° C. Found: C, 60.45; H, 6.72; N, 15.35. $C_{14}H_{17}N_3O_2.H_2O$ requires: C, 60.63; H, 6.91; N, 15.15%.

EXAMPLE 33

1-[2-(4-Ureidomethylphenoxy)ethyl]imidazole

1-[2-(4-Aminomethylphenoxy)ethyl]imidazole (1.1 g) was dissolved in 1N hydrochloric acid (7 ml) and a solution of potassium cyanate (0.5 g) in 1 ml of water was added. The solution was allowed to stand at room temperature for 30 minutes and then warmed briefly to 100° C. and cooled. The resulting solid was filtered off and crystallised twice from water to give 1-[4-(2-ureidomethylphenoxy)ethyl]imidazole (0.33 g), m.p. 198°–199° C. Found: C, 59.24; H, 6.13; N, 21.96. $C_{13}N_{16}N_2O_2$ requires: C, 59.98; H, 6.20; N, 21.53%.

EXAMPLE 34

1-[2-(4-Acetylcarbamoylphenoxy)ethyl]imidazole

N,N'-Carbonyldiimidazole (4.9 g) was dissolved in dry N,N-dimethylformamide (10 ml) and acetic acid (1.8 g) was added. The solution was stirred for 5 minutes and then 1-[2-(4-carbamoylphenoxy)ethyl]imidazole (4.6 g) was added. The solution was heated under reflux for 3 hours and then evaporated. The residue was treated with aqueous sodium bicarbonate and the mixture was extracted several times with ethyl acetate. The combined ethyl acetate extracts were washed with water, dried ($Na_2SO_4$) and evaporated to give an oil which was chromatographed on silica gel. Elution with chloroform gave some impurity. Further elution with chloroform/methanol (50:1) gave a solid which was crystallised from 2-butanone to give 1-[2-(4-acetylcarbamoylphenoxy)ethyl]imidazole (0.9 g), m.p. 164°–165° C. Found: C, 61.28; H, 5.54; N, 15.51. $C_{14}H_{15}N_3O_3$ requires: C, 61.53; H, 5.53; N, 15.38%.

EXAMPLE 35

1-[2-(4-Benzoylcarbamoylphenoxy)ethyl]imidazole

Treatment of benzoic acid with N,N'-carbonyldiimidazole and 1-[2-(4-carbamoylphenoxy)ethyl]imidazole in dry N,N-dimethylformamide as described in Example 34 gave 1-[2-(4-benzoylcarbamoylphenoxy)ethyl]imidazole, m.p. 152°–154° C. (from methanol/ethyl acetate). Found: C, 67.66; H, 5.16; N, 12.59. $C_{19}H_{17}N_3O_3$ requires: C, 68.05; H, 5.11; N, 12.53%.

EXAMPLE 36

N-Methylsulphonyl-4-[2-(1-imidazolyl)ethoxy]benzenecarboximidic acid

A mixture of 1-[2-(4-carboxyphenoxy)ethyl]imidazole (3.3 g) (formed from the hydrochloride salt by dissolving in water, making the solution just alkaline with dilute sodium hydroxide followed by precipitation by addition of acetic acid) and N,N'-carbonyldiimidazole (3.0 g) was heated on a steam bath for 2 hours and then methanesulphonamide (3.2 g) was added. The mixture was heated at 150° C. for 2½ hours, and then cooled slightly and taken up in the minimum volume of ethanol. The solid which precipitated on cooling was filtered off and washed with water to give N-methylsulphonyl-4-[2-(1-imidazolyl)ethoxy]benzenecarboxamidic acid, m.p. 198°–199° C. Found: C, 50.37; H, 4.84; N, 13.67. $C_{13}H_{15}N_3O_4S$ requires: C, 50.47; H, 4.89; N, 13.59%.

EXAMPLE 37

N-Benzenesulphonyl-4-[2-(1-imidazolyl)ethoxy]benzenecarboximidic acid

Treatment of 1-[2-(4-carboxyphenoxy)ethyl]imidazole with N,N'-carbonyldiimidazole followed by benzenesulphonamide as described in Example 36 above gave N-benzenesulphonyl-4-[2-(1-imidazolyl)ethoxy]benzenecarboximidic acid, m.p. 250°–252° C. (from N,N-dimethylformamide/$H_2O$). Found: C, 58.17; H, 4.60; N, 11.08. $C_{18}H_{17}N_3O_4S$ requires: C, 58.21; H, 4.61; N, 11.31%.

EXAMPLE 38

1-[3-(4-Carboxyphenoxy)propyl]imidazole

A. Sodium hydride (0.6 g, 50% suspension in mineral oil) was added cautiously to a stirred and cooled solution of imidazole (0.79 g) in dry N,N-dimethylformamide (50 ml). After the initial vigorous reaction had subsided the mixture was heated to 100° C. for 10 minutes and then stirred at room temperature for a further 1 hour. Ethyl 4-(3-chloropropoxy)benzoate (2.8 g) was added over 2 minutes and the resulting mixture was heated on a steam bath for 6 hours and then cooled. Water (1 ml) was added to decompose any unreacted sodium hydride and the solution was evaporated and the residue was chromatographed on silica gel. Elution with chloroform gave mineral oil and small amounts of impurity. Elution with chloroform/methanol (20:1) gave the pure 1-[3-(4-ethoxycarbonylphenoxy)propyl]imidazole as an oil on evaporation of the solvent.

B. The ester (0.75 g) was added to a solution of potassium hydroxide (2.0 g) in water (20 ml) and the mixture was heated on a steam bath for 18 hours and then cooled. Acidification with acetic acid gave a solid which was filtered off and crystallised from water to give 1-[3-(4-carboxyphenoxy)propyl]imidazole (0.31 g), m.p. 218° C. Found: C, 63.11; H, 5.77; N, 11.18. $C_{13}H_{14}N_2O_3$ requires: C, 63.41; H, 5.69; N, 11.38%.

EXAMPLE 39

1-[2-(2-Carbamoylmethylphenoxy)ethyl]imidazole

A mixture of 1-[2-(2-carbethoxymethylphenoxy)ethyl]imidazole (3.5 g) concentrated aqueous ammonia (30 ml) and ethanol (10 ml) was heated at 120° C. for 18 hours in a pressure vessel. The mixture was cooled and evaporated and the oily residue chromatographed on silica gel. Elution with chloroform/methanol (4:1) gave a solid which was crystallised from isopropanol/ethyl acetate to give 1-[2-(2-carbamoylmethylphenoxy)ethyl]imidazole (0.7 g), m.p. 116°–118° C. Found: C, 63.42; H, 6.10; N, 16.82. $C_{13}H_{15}N_3O_2$ requires: C, 63.66; H, 6.16; N, 17.13%.

EXAMPLE 40

N-Cyano-4-[2-(1-imidazolyl)ethoxy]benzenecarboximidic acid

Treatment of 1-[2-(4-carboxyphenoxy)ethyl]imidazole with N,N'-carbonyldiimidazole followed by cyanamide as described in Example 36 above gave N-cyano-4-[2-(1-imidazolyl)ethoxy]benzenecarboximidic acid, m.p. 199°–200° C. (d) (from water). Found: C, 60.59; H, 4.64; N, 22.20. $C_{13}H_{12}N_4O_2$ requires: C, 60.93; H, 4.72; N, 21.87%.

EXAMPLE 41

1-[2-(4-Carboxyphenoxy)ethyl]imidazole (1 g) was added to distilled water (900 ml) and the pH adjusted to 5 with hydrochloric acid. Sodium chloride (18 g) was added and the solution made up to 2 liters. The final solution was sterilised by filtration through a bacteria-proof filter under aseptic conditions into 10 ml glass vials so as to comply with the test for sterility of Appendix 121 British Pharmacopea 1973.

EXAMPLE 42

Capsules are compounded from the following ingredients:

|  | mg/capsule |
|---|---|
| 1-[2-(4-carboxyphenoxy)ethyl]imidazole | 20 |
| Lactose | 250 |
| Maize starch | 75 |
| Magnesium stearate | 5 |
|  | 350 mg |

The ingredients are thoroughly blended, granulated and the filtered into hard gelatine capsules of the desired size.

I claim:

1. A compound of the formula $$N \overset{\frown}{\underset{\smile}{\phantom{N}}} N-(CH_2)_n-O-\underset{R^1}{\overset{R}{\bigcirc}} \quad (I)$$

or the pharmaceutically acceptable acid addition salt thereof, wherein:

R is $CONHR^3$ or $CON(R^4)_2$;

$R^1$ is H, $C_1$–$C_4$ alkoxy or halogen;

$R^3$ is H, $C_1$–$C_4$ alkyl, $C_1$–$C_4$ alkanoyl, $C_1$–$C_4$ alkylsulphonyl, CN, benzoyl or benzenesulphonyl, or a monosubstituted benzoyl or benzenesulphonyl, the monosubstitutent being $C_1$–$C_4$ alkyl, $C_1$–$C_4$ alkoxy, $CF_3$ or halogen;

each $R^4$ is $C_1$–$C_4$ alkyl or the two $R^4$ groups together with the nitrogen atom to which they are attached form a pyrrolidino, piperidino or morpholino group;

$R^5$ is H, $C_1$–$C_4$ alkanoyl, $C_1$–$C_4$ alkoxycarbonyl, carbamoyl, $C_1$–$C_4$ alkyl carbamoyl;

and n is 2 or 3.

2. A compound of claim 1 wherein n is 2.

3. A compound of claim 1 wherein $R^1$ is H.

4. A compound of claim 1 wherein R is an N-(mono or di-methyl)carbamoyl group.

5. A compound of claim 4 wherein said N-(mono or dimethyl)carbamoyl group is at the 4- position.

6. 1-[2-(4-N-Methylcarbamoylphenoxy)ethyl]imidazole according to claim 1.

7. 1-[2-(4-N,N-Dimethylcarbamoylphenoxy)ethyl]imidazole according to claim 1.

8. A pharmaceutical composition for use as an inhibitor of thromboxane synthetase enzyme, comprising an effective amount of a compound of claim 1 or a pharmaceutically acceptable acid addition salt thereof together with a pharmaceutically acceptable diluent or carrier.

9. A method of selectively inhibiting the thromboxane synthetase enzyme in an animal, which comprises: administering an effective amount of a compound of claim 1 or the pharmaceutically acceptable acid addition salt thereof or of a pharmaceutical composition of claim 8.

* * * * *